(12) United States Patent
Chattopadhyay et al.

(10) Patent No.: US 7,579,491 B2
(45) Date of Patent: Aug. 25, 2009

(54) PROCESS FOR PREPARING BREVIFOLIOL

(75) Inventors: Sunil Kumar Chattopadhyay, Uttar Pradesh (IN); Sachin Srivastava, Uttar Pradesh (IN); Arvind Singh Negi, Uttar Pradesh (IN); Ranganathan Santha Kumar Tirupadiripuliyur, Pradesh (IN); Ankur Garg, Uttar Pradesh (IN); Suman Preet Singh Khanuja, Uttar Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 16 days.

(21) Appl. No.: 11/548,166

(22) Filed: Oct. 10, 2006

(65) Prior Publication Data

US 2008/0039641 A1    Feb. 14, 2008

Related U.S. Application Data

(63) Continuation of application No. 10/334,678, filed on Dec. 30, 2002, now abandoned.

(51) Int. Cl.
*C07D 305/00*    (2006.01)
*A61K 36/13*    (2006.01)

(52) U.S. Cl. .................... 549/510; 424/769
(58) Field of Classification Search ............. 549/510; 424/769; 514/510, 183, 449, 453
See application file for complete search history.

(56) References Cited

U.S. PATENT DOCUMENTS 5,475,120 A    12/1995    Rao
5,480,639 A    1/1996    ElSohly et al.

FOREIGN PATENT DOCUMENTS

WO    WO-01/36007 A2    5/2001

OTHER PUBLICATIONS

Jun'ichi Kobayashi, et al., "Effects of Taxoids from Taxus Cispidata on Microtubule Depolymerization and Vincristing Accumulation in MDR Cells", Bioorganic & Medicinal chemistry Lettrs, Oxford, GB, vol. 7, No. 4, Feb. 1997, pp. 393-398.

H. Morita, et al., "3D QSAR Analysis of Taxoids from Taxus Cuspidata Var. NANA by comparative Molecular Field Approach", Bioorganic & Medicinal Chemistry Letters, Oxford GB, vol. 7, No. 18, Sep. 1997, pp. 2387-2392.

Felipe Balza, et al., "Brevifoliol, A Taxane From Taxus Brevifolla", Phytochemistry, Pergamon Press, GB, vol. 30, No. 5, 1991, pp. 1613-1614.

Gunda I. Georg, et al., "A Reinvestigation of the Taxol Content of Himalayan Taxus Wallichiana Zucc, and a Revision fo the Structure of Brevifoliol", Biooragnic & Medicinal Chemistry Letters, vol. 3, No. 6, 1993, pp. 1345-1348.

*Primary Examiner*—Janet L. Andres
*Assistant Examiner*—Raymond Covington
(74) *Attorney, Agent, or Firm*—Darby & Darby

(57) ABSTRACT

The present invention provides a process for production of an anticancer taxoid brevifoliol of the formula I

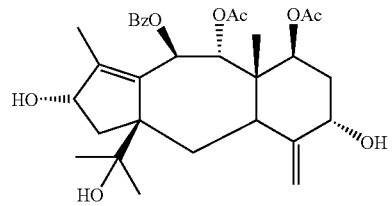

Formula 1 from plants belonging to the genus *Taxus* by first extracting the dried and pulverized leaves of the plant with an alcohol preferably at a temperature in the range of 20-40° C. and then. concentrating the solvent to obtain an alcoholic extract. The alcoholic extract obtained is then adsorbed with an adsorbent and the resulting adsorbed material is then dried at a temperature ranging from 20-50° C. for 4-48 hours. The dried adsorbed material is then extracted with a combination of an aliphatic solvent and a chlorinated solvent successively and concentrated to obtain a residue. The residue is subjected to gross fractionation using column chromatography such as silica gel, florosil and silicic acid followed by chromatography with a suitable adsorbent to get brevifoliol.

25 Claims, No Drawings

PROCESS FOR PREPARING BREVIFOLIOL

FIELD OF THE INVENTION

The present invention relates to a process for preparing brevifoliol which is useful as an anticancer agent. Particularly, the present invention relates to a processing technology for the isolation of brevifoliol of formula (1) from plants of genus *Taxus*. More particularly, this invention relates to a processing technology for the isolation of brevifoliol from the leaves of the plant *Taxus wallichiana*.

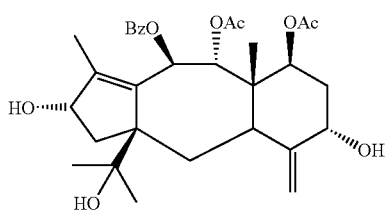

Formula 1

BACKGROUND OF THE INVENTION

Brevifoliol was first isolated from the leaves of the plant *Taxus brevifolia* (F. Balza et al Phytochemistry 30, p. 1613-1614 (1991)). The process of its isolation involved extracting the fresh leaves of *Taxus wallichiana* with ethyl alcohol to get an extract. The crude extract after concentration was diluted with water and partitioned between hexane, chloroform and ethyl acetate sequentially. The chloroform extract upon concentration yielded a dark brown residue. The resultant residue was subjected to column chromatography over silica gel and eluted with chloroform and chloroform-methanol gradient. Six fractions were collected and brevifoliol was isolated from fraction five by rechromatography over silica gel and eluting with hexane-ethyl acetate gradient.

Brevifoliol has been isolated from other species of *Taxus* including the Himalayan yew *Taxus wallichiana* which is available in India., Recently, the structure of brevifoliol has been revised and it was shown to belong to 11 (15→1) abeo taxoid bicyclic skeleton of formula (1). The isolation of brevifoliol from leaves of the plant *Taxus wallichiana* is also reported in S. K. Chattopadhyay et al Indian J. Chemistry 35B, 175-177(1996) as part of studies on the isolation of anticancer compounds. The process of this disclosure involved extracting the dried and crushed needles of *Taxus wallichiana* with methanol for 72 hours and the extract was concentrated in vacuo. The concentrate was diluted with water and extracted with hexane and chloroform respectively. Concentration of the chloroform phase under vacuum left a residue which was separated by column chromatography over silica gel. Fraction eluted with chloroform-methanol (98:5) contained brevifoliol which was further purified by re-chromatography over silica gel and eluted with chloroform-methanol (99:2). Fractions containing brevifoliol were combined and concentrated and recrystallized from pet-ether and ethyl acetate mixture to get brevifoliol as needles. In in vitro testing of brevifoliol, it was found to have significant anticancer activity against different cancer cell lines. The detection of anticancer activity in brevifoliol prompted the present investigators to develop an efficient processing technology for isolation of the compound in large quantities from the needles of the plant for further biological testing.

The prior art process of isolation of brevifoliol suffers from a number of disadvantages including partitioning of the aqueous extract with hexane and chloroform and repeated column chromatography to get the compound. Although the partitioning of the aqueous phase with organic solvents works on small scale, it forms thick emulsions on large scale partitioning process and creates hindrance in getting the fractions separated. Also, the use of repeated chromatography might be useful on small-scale isolation of brevifoliol, it is only cumbersome, tedious and not economical on large-scale process.

OBJECTS OF THE INVENTION

The main object of the present invention is to provide a process for the production of an important taxoid brevifoliol with anticancer activity from the needles of the plants belonging to the genus *Taxus*.

Another object of the present invention is to develop a processing technology for isolation of brevifoliol from the leaves of the plant *Taxus wallichiana*.

Still another object of the present invention is to develop a processing technology for production of brevifoliol which does not use any water partitioning for isolation of brevifoliol from the needles of plants of genus *Taxus*.

Another object of the present invention is to isolate brevifoliol from the leaves of the plant *Taxus* with high yield.

Still another object of the present invention is to develop a processing technology for isolation brevifoliol in a cost effective manner.

Yet another object of the present invention is to develop a processing technology suitable for isolation of brevifoliol on large scale.

SUMMARY OF THE INVENTION

The present invention provides a process for the production of an anticancer compound brevifoliol from plants belonging to genus *Taxus*. The present invention provides a process for the production of brevifoliol from the needles of the plant *Taxus wallichiana*.

Accordingly, the present invention provides a process for preparing brevifoliol, an anticancer compound of formula 1

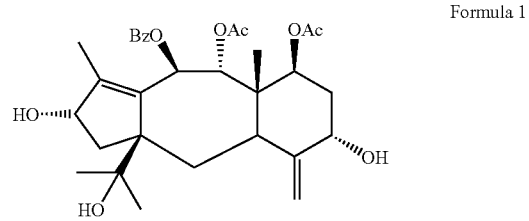

Formula 1 from plants belonging to the genus *Taxus* comprising
(i) extracting the dried and pulverized leaves of the plant with an alcohol and concentrating the solvent to obtain an alcoholic extract,
(ii) adsorbing the alcoholic extract with an adsorbent and drying the adsorbed material,
(iii) extracting the adsorbed material with an aliphatic solvent and then with a chlorinated solvent successively and concentrating the chlorinated solvent to obtain a residue,
(iv) subjecting the residue to gross fractionation using column chromatography, followed by
(v) chromatography with an adsorbent to get brevifoliol.

In one embodiment of the present invention, the plants are selected from the groups comprising of *Taxus wallichiana*, *Taxus baccata* and *Taxus brevifolia*.

In another embodiment of the invention, the extraction in step (i) above is carried out at a temperature in the range of 20 to 40° C.

In yet another embodiment of the invention, the drying of the adsorbed material in step (ii) above is carried out at a temperature ranging from 20-50° C. and for a time period in the range of 4-48 hours.

In another embodiment of the invention, the alcohol used in step (i) is an alkanol selected from the group comprising of methanol and ethanol.

In still another embodiment of the invention, the adsorbent material used in step (ii) is selected from the group comprising of celite, cellulose and a mixture thereof.

In a further embodiment of the invention, the adsorbent material is celite.

In yet another embodiment of the invention, the aliphatic solvent used in step (iii) is selected from the group comprising of hexane and petroleum ether.

In a further embodiment of the invention, the aliphatic solvent is petroleum ether.

In another embodiment of the invention, the chlorinated solvent used in step (iii) is selected from the group comprising of chloroform and dichloromethane.

In a further embodiment of the invention, the chlorinated solvent is chloroform.

In another embodiment of the invention, gross fractionation of the residue is carried out by column chromatography selected from the group comprising of silica gel, florosil and silicic acid.

In a further embodiment of the invention, silica gel chromatography was used.

In yet another embodiment of the invention, the adsorbent used in step (v) is selected from the group comprising of silica gel, florosil, silicic acid and alumina.

In a further embodiment of the invention, the adsorbent is alumina.

The present invention also provides a process for the production of an anticancer compound brevifoliol of formula 1

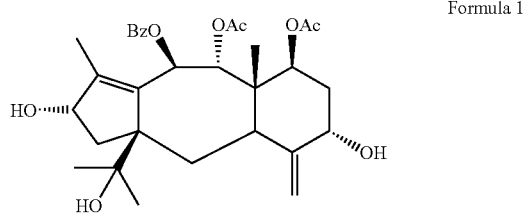

Formula 1 from the plant *Taxus wallichiana*, comprising
(i) extracting the dried and pulverized leaves of the plant with an alcohol at 20-40° C. and concentrating the solvent to obtain an alcoholic extract,
(ii) adsorbing the alcoholic extract with an adsorbent and drying the adsorbed material at a temperature ranging from 20-50° C. for 4-48 hours,
(iii) extracting the adsorbed material with an aliphatic solvent and then with a chlorinated solvent successively and concentrating the chlorinated solvent to a residue and
(iv) subjecting the residue to gross fractionation using column chromatography, followed by
(v) chromatography with an adsorbent to get brevifoliol.

In one embodiment of the invention, the alcohol used is an alkanol selected from the group comprising of methanol and ethanol.

In still another embodiment of the invention, the adsorbent material is selected from the group comprising of celite, cellulose and a mixture thereof.

In a further preferred embodiment of the invention, the adsorbent material is celite.

In yet another embodiment of the invention, the aliphatic solvent is selected from the group comprising of hexane and petroleum ether.

In a further embodiment of the invention, the aliphatic solvent is petroleum ether.

In another embodiment of the invention, the chlorinated solvent is selected from the group comprising of chloroform and dichloromethane.

In a further embodiment of the invention, the chlorinated solvent is chloroform.

In still another embodiment of the invention, the gross fractionation of the chloroform extract is done using chromatography selected from the group comprising of silica gel, florosil and silicic acid.

In a further embodiment of the invention, silica gel chromatography was used.

In yet another embodiment of the invention, the adsorbent is selected from the group comprising of silica gel, florosil, silicic acid and alumina.

In a further embodiment of the invention, the suitable adsorbent is alumina.

DETAILED DESCRIPTION OF THE INVENTION

The present invention provides a process for the production of an anticancer compound brevifoliol of formula 1

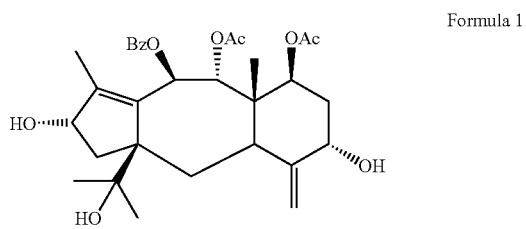

Formula 1 from plants belonging to the genus *Taxus* by first extracting the dried and pulverized leaves of the plant with an alcohol preferably at a temperature in the range of 20-40° C. and then, concentrating the solvent to obtain an alcoholic extract. The alcoholic extract obtained is then adsorbed with an adsorbent and the resulting adsorbed material is then dried at a temperature ranging from 20-50° C. for 4-48 hours. The dried adsorbed material is then extracted with a combination of an aliphatic solvent and a chlorinated solvent successively and concentrated to obtain a residue. The residue is subjected to gross fractionation using column chromatography such as silica gel, florosil and silicic acid followed by chromatography with a suitable adsorbent to get brevifoliol.

The plants are preferably chosen from high yielding varieties of the species *Taxus*, such as *Taxus wallichiana*, *Taxus baccata* and *Taxus brevifolia*.

The alkanol used is preferably methanol or ethanol. The adsorbent used adsorbing the alcoholic extract is selected from celite or cellulose or a mixture thereof, preferably celite. The aliphatic solvent used can be either hexane or petroleum ether, preferably petroleum ether, while the chlorinated solvent used is chloroform or dichloromethane, preferably chloroform. In a preferred embodiment of the present invention, silica gel chromatography is used for gross fractionation of the chlorinated residue. The adsorbent used for the separation of the final product is selected from silica gel, florosil, silicic acid and alumina, preferably alumina.

In one embodiment the present invention provides a process for the production of an anticancer compound brevifoliol of formula 1 from the plant *Taxus wallichiana* comprising of (i) extracting the dried and pulverized leaves of the plant with an alcohol at 20-40° C. and concentrating the solvent to obtain an alcoholic extract, (ii) adsorbing the alcoholic extract with an adsorbent and drying the adsorbed material at a temperature ranging from 20-50° C. for 4-48 hours, (iii) extracting the adsorbed material with an aliphatic solvent and then with a chlorinated solvent successively and concentrating the chlorinated solvent to a residue and (iv) subjecting the residue to gross fractionation using column chromatography, followed by (v) chromatography with a suitable adsorbent to get brevifoliol.

The yield of brevifoliol obtained by the process of the present invention using the plant *Taxus wallichiana* was found to be 0.06% by weight, which is six times higher than the yield obtained from the leaves of the same plant using prior art solvent partitioning method disclosed in S. K. Chattopadhyay, et al, Indian J. Chemistry 35B, 175-177(1996). It is to be noted that if high brevifoliol yielding plants are used, the yield is higher. The process of the present invention is useful for all such varieties and produces better yield than so far reported in the prior art for recovery of brevifoliol from plant sources.

The following examples describe the process of the invention and are provided to illustrate the invention and should not be construed to limit the scope of the invention.

EXAMPLE 1

Air-dried and pulverized leaves of the plant *Taxus wallichiana* (3 kgs) were extracted with MeOH (9 lit. times 0.3) at 20-40° C.) for three days. MeOH was concentrated under vacuum and the MeOH ext.was adsorbed with celite (800 g) and the adsorbed material was dried at 20-50° C. for 4-48 hours. The dried adsorbed material was then extracted with petroleum ether (60-80° C.) (3 lit. times 3) and chloroform (3 lit. times.3) successively. Chloroform extract (80 g) was concentrated under vacuum to a residue and was fractionated over a bed of silica gel (400 g) using chloroform and 2% MeOH in chloroform. The fraction of the later elunt was concentrated and chromatographed over a bed of alumina (100 g.) in pet.ether. Brevifoliol was eluted from the column with 10% ethyl acetate in pet. ether as amorphous solid which was recrystallized from pet.ether-ethyl acetate as needles (1.8 g.).

EXAMPLE 2

Air-dried and pulverized leaves of the plant *Taxus wallichiana* (3 kgs) were extracted with EtOH (9 lit. times.3) at 20-40° C.) for three days. EtOH was concentrated under vacuum and the EtOH ext. was adsorbed with cellulose (800 g) and the adsorbed material was dried at 20-50° C. for 4-48 hours. The dried adsorbed material was then extracted with petroleum ether (60-80° C.) (3 lit. times. 3) and dichloromethane (3 lit. times 3) successively. Dichloromethane extract (80 g) was concentrated under vacuum to a residue and was fractionated over a bed of silica gel (400 g) using dichloromethane and 2% MeOH in dichloromethane. The fraction of the latter eluant was concentrated and chromatographed over a bed of alumina (100 g) in pet.ether. Brevifoliol was eluted from the column with 10% ethyl acetate in pet. ether as amorphous solid which was recrystallized from pet.ether-ethyl acetate as needles (1.8 g.).

EXAMPLE 3

Air-dried and pulverized leaves of the plant *Taxus wallichiana* (3 kgs) were extracted with MeOH (9 lit. times 3 at 20-40° C.) for three days. MeOH was concentrated under vacuum and the MeOH ext. was adsorbed with mixture of celite-cellulose (800 g) and the adsorbed material was dried at 20-50° C. for 4-48 hours. The dried adsorbed material was then extracted with petroleum ether (60-80° C.) (3 lit. times 3) and chloroform (3 lit. times 3) successively. Chloroform extract (80 g) was concentrated under vacuum to a residue and was fractionated over a bed of silica gel (400 g) using chloroform and 2% MeOH in chloroform. The fraction of the later eluant was concentrated and chromatographed over a bed of alumina (100 g) in pet.ether. Brevifoliol was eluted from the column with 10% ethyl acetate in pet. ether as amorphous solid which was recrystallized from pet.ether-ethyl acetate as needles (1.8 g.).

ADVANTAGES OF THE INVENTION

1. The extraction process described in this invention does not use any extreme conditions of temperature and pressure, thus it can be adaptable to commercial production of brevifoliol.
2. The solvents used in extraction process can be recycled and thus the process would be cost effective.
3. No water partitioning is used to isolate brevifoliol in this process and thus the process will be suitable for large scale extraction of brevifoliol and cost effective
4. With the availability of high brevifoliol yielding plants which are available globally, the process of the present invention can yield better than the best yield so far reported for brevifoliol from higher plants.

What is claimed is:

1. A process for preparing brevifoliol, an anticancer compound of formula 1

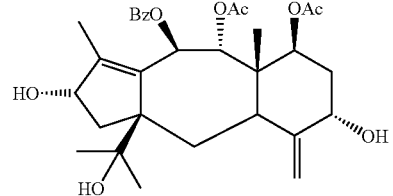

Formula 1 from plants belonging to the genus *Taxus* comprising (i) extracting the dried and pulverized leaves of the plant with an alcohol and concentrating the solvent to obtain an alcoholic extract, (ii) adsorbing the alcoholic extract with an adsorbent and drying the adsorbed material wherein the absorbent is chosen from the group consisting of celite, cellulose and mixtures thereof, (iii) extracting the adsorbed material with an aliphatic solvent and then with a chlorinated solvent successively and concentrating the chlorinated solvent to obtain a residue, (iv) subjecting the residue to gross fractionation using column chromatography, followed by (v) chromatography with an adsorbent to get brevifoliol;

with the proviso that the method does not involve a water partitioning step for the production of brevifoliol.

2. A process as claimed in claim 1 wherein the plants are selected from the groups consisting of *Taxus wallichiana, Taxus baccata* and *Taxus brevifolia.*

3. A process as claimed in claim 1 wherein the extraction in step (i) above is carried out at a temperature in the range of 20 to 40° C.

4. A process as claimed in claim 1 wherein the drying of the adsorbed material in step (ii) above is carried out at a temperature ranging from 20-50° C. and for a time period in the range of 4-48 hours.

5. A process as claimed in claim 1 wherein the alcohol used in step (i) is an alkanol selected from the group consisting of methanol and ethanol.

6. A process as claimed in claim 1 wherein the adsorbent material is celite.

7. A process as claimed in claim 1 wherein the aliphatic solvent used in step (iii) is selected from the group consisting of hexane and petroleum ether.

8. A process as claimed in claim 7 wherein the aliphatic solvent is petroleum ether.

9. A process as claimed in claim 1 wherein the chlorinated solvent used in step (iii) is selected from the group consisting of chloroform and dichloromethane.

10. A process as claimed in claim 9 wherein the chlorinated solvent is chloroform.

11. A process as claimed in claim 1 wherein the gross fractionation of the residue is carried out by column chromatography selected from the group consisting of silica gel, florosil and silicic acid.

12. A process as claimed in claim 11 wherein the silica gel chromatography was used.

13. A process as claimed in claim 1 wherein the adsorbent used in step (v) is selected from the group consisting of silica gel, florosil, silicic acid and alumina.

14. A process as claimed in claim 13 wherein the adsorbent is alumina.

15. A process for the production of an anticancer compound brevifoliol of formula 1

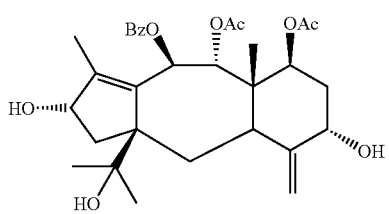

Formula 1 from the plant *Taxus wallichiana*, comprising (i) extracting the dried and pulverized leaves of the plant with an alcohol at 20-40° C. and concentrating the solvent to obtain an alcoholic extract, (ii) adsorbing the alcoholic extract with an adsorbent and drying the adsorbed material at a temperature ranging from 20-50° C. for 4-48 hours wherein the absorbent is chosen from the group consisting of celite, cellulose and mixtures thereof, (iii) extracting the adsorbed material with an aliphatic solvent and then with a chlorinated solvent successively and concentrating the chlorinated solvent to a residue and (iv) subjecting the residue to gross fractionation using column chromatography, followed by (v) chromatography with an adsorbent to get brevifoliol;

with the proviso that the method does not involve a water partitioning step for the production of brevifoliol.

16. A process as claimed in claim 15 wherein the alcohol used is an alkanol selected from the group consisting of methanol and ethanol.

17. A process as claimed in claim 15 wherein the adsorbent material used in step (ii) is celite.

18. A process as claimed in claim 15 wherein the aliphatic solvent is selected from the group consisting of hexane and petroleum ether.

19. A process as claimed in claim 18 wherein the aliphatic solvent is petroleum ether.

20. A process as claimed in claim 15 wherein the chlorinated solvent is selected from the group consisting of chloroform and dichloromethane.

21. A process as claimed in claim 20 wherein the chlorinated solvent is chloroform.

22. A process as claimed in claim 15 wherein the gross fractionation of the chloroform extract is done using chromatography selected from the group consisting of silica gel, florosil and silicic acid.

23. A process as claimed in claim 22 wherein silica gel chromatography was used.

24. A process as claimed in claim 15 wherein the adsorbent used in step (v) is selected from the group consisting of silica gel, florosil, silicic acid and alumina.

25. A process as claimed in claim 24 wherein the adsorbent is alumina.

\* \* \* \* \*